US00PP24983P2

(12) United States Plant Patent
Bergman

(10) Patent No.: US PP24,983 P2
(45) Date of Patent: Oct. 21, 2014

(54) *CHRYSANTHEMUM* PLANT NAMED 'CIDZ0047'

(50) Latin Name: *Chrysanthemum×morifolium*
Varietal Denomination: CIDZ0047

(71) Applicant: Syngenta Crop Protection AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 86 days.

(21) Appl. No.: 13/815,113

(22) Filed: Jan. 31, 2013

(51) Int. Cl.
*A01H 5/00* (2006.01)

(52) U.S. Cl.
USPC ..... Plt./288

(58) Field of Classification Search
USPC ..... Plt./288, 287
See application file for complete search history.

*Primary Examiner* — Susan McCormick Ewoldt
(74) *Attorney, Agent, or Firm* — Joshua L. Price

(57) ABSTRACT

A new *Chrysanthemum* plant named 'CIDZ0047' particularly distinguished by pure white decorative-type inflorescences, both quill and spoon-shaped ray floret forms can be found with the spoon-shaped more profound on warmer grown crops, strong and uniform plant habit, suitable for production with both disbudded or no bud removal.

1 Drawing Sheet

Latin name of the genus and species of the plant claimed: *Chrysanthemum×morifolium.*

Varietal denomination: 'CIDZ0047'.

BACKGROUND OF THE NEW PLANT

The present invention comprises a new *Chrysanthemum*, botanically known as *Chrysanthemum×morifolium*, and hereinafter referred to by the variety name 'CIDZ0047'.

'CIDZ0047' is a product of a planned breeding program. The new cultivar has pure white decorative-type inflorescences, both quill and spoon-shaped ray floret forms can be found with the spoon-shaped more profound on warmer grown crops, strong and uniform plant habit, suitable for production with both disbudded or no bud removal.

'CIDZ0047' originated from a hybridization made in February 2008 in a greenhouse in Bogota, Columbia. The female parent was the proprietary plant designated 'Yovail', U.S. Plant Pat. No. 18,298, with flat ray florets and a more compact plant habit.

The male parent of 'CIDZ0047' was the unpatented, proprietary plant designated as 'B3122' with flat-type yellow ray florets, produces more disc florets and pollen when compared to 'CIDZ0047'. The resultant seed was sown and grown in a shade structure in July 2008 in Fort Myers, Fla. USA.

'CIDZ0047' was selected as one flowering plant within the progeny of the stated cross in December 2008 in a shade structure in Fort Myers, Fla.

The first act of asexual reproduction of 'CIDZ0047' was accomplished when vegetative cuttings were propagated from the initial selection in February 2009 in a greenhouse in Fort Myers, Fla.

BRIEF SUMMARY OF INVENTION

Horticultural examination of plants grown from cuttings of the plant initiated in February 2009, and continuing thereafter, has demonstrated that the combination of characteristics as herein disclosed for 'CIDZ0047' are firmly fixed and are retained through successive generations of asexual reproduction.

'CIDZ0047' has not been observed under all possible environmental conditions. The phenotype may vary significantly with variations in environment such as temperature, light intensity and day length.

A Plant Breeder's Right for this cultivar was applied for in Canada on Jun. 29, 2012 (12-7651). 'CIDZ0047' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0047' with colors being as true as possible with an illustration of this type.

The photographic drawing shows in FIG. 1 four flowering plants of the new variety growing in one container and the inset a close-up of the inflorescences.

DETAILED BOTANICAL DESCRIPTION

The plant descriptions, measurements and aforementioned photographs were taken in Gilroy, Calif. in early October 2012 under natural light. These plants were grown 4 plants, disbudded, in a 6-inch container, in a greenhouse in Nipomo, Calif. These plants used in the photograph and descriptions were about 10-12 weeks old.

Color references are made to The Royal Horticultural Society Colour Chart (R.H.S.) 2001.

TABLE 1

DIFFERENCES BETWEEN THE NEW VARIETY 'CIDZ0047' AND A MOST SIMILAR VARIETY

| | 'CIDZ0047' | 'Yogainsville' (U.S. Plant Pat. No. 13,033) |
|---|---|---|
| Ray floret type: | Has more quilled | Has fewer quilled |
| Plant habit: | More compact and shorter | Less compact and taller |
| Color retention: | Maintains pure white when grown under cooler conditions | Develops some pink hues under cooler conditions |

Plant:

*Form, growth and habit*.—Herbaceous pot-type, stems upright, uniform and strong growth habit.

*Plant height*.—23-25.0 cm.

*Plant height* (*inflorescence included*).—25-27.0 cm.

*Plant width*.—15-20.0 cm.

Roots:

*Number of days to initiate roots*.—About 4 days at about 22 degrees C.

*Number of days to produce a rooted cutting*.—4-6 days at 22 degrees C.

*Type*.—Fine, fibrous, free branching.

*Color*.—RHS N155B but whiter.

Foliage:

*Arrangement*.—Alternate.

*Immature, leaf color, upper surface*.—Closest to RHS 147A.

*Immature, leaf color, lower surface*.—Closest to RHS 147B.

*Mature, leaf color, upper surface*.—Closest to RHS 137A with some a little darker.

*Mature, lean color, lower surface*.—Closest to RHS 137C.

*Length*.—7.2-8.2 cm.

*Width*.—3.9-5.1 cm.

*Shape*.—Ovate.

*Base shape*.—Attenuate.

*Apex shape*.—Mucronulate.

*Margin*.—Most are palmately lobed though some are not quite; slightly dentate.

*Texture, upper surface*.—Bifid T-shaped hairs.

*Texture, lower surface*.—Bifid T-shaped hairs.

*Color of veins, upper surface*.—RHS 144B.

*Color of veins, lower surface*.—RHS 144B.

*Pattern of veining*.—Palmately.

*Petiole color*.—RHS 144B.

*Petiole length*.—1.2-1.5 cm.

*Petiole diameter*.—0.2-0.5 cm.

*Petiole texture*.—Bifid T-shaped hairs.

Stem:

*Quantity of main branches per plant*.—3-4.

*Color of stem*.—RHS 137A.

*Length of stem*.—19-23.0 cm.

*Diameter*.—0.4 cm.

*Length of internodes*.—0.5-1.0 cm.

*Texture*.—Bifid T-shaped hairs.

*Color of peduncle*.—RHS 137A.

*Length of peduncle*.—3.0-3.5 cm.

*Peduncle diameter*.—0.25-3.0 cm.

*Texture*.—Bifid T-shaped hairs.

Inflorescence:

*Type*.—Compositae type, solitary inflorescences borne terminally above foliage, ray florets arranged acropetally on a capitulum.

*Quantity of short days to flowering* (*response time*).—About 54 days.

*Natural season flowering*.—Not determined on this variety.

*Quantity of inflorescences per plant*.—3-4.

*Lastingness of individual blooms on the plant*.—About 4 weeks.

*Fragrance*.—Slightly spicy.

Bud (just when opening/showing color):

*Color*.—Closest to RHS 155D but pure white.

*Length*.—1.5-2.0 cm.

*Width*.—1.5 cm.

*Shape*.—Oblate.

Immature inflorescence:

*Diameter*.—7.5 cm when flattened out.

*Color of ray florets, upper surface*.—Closest to RHS 155D but pure white.

*Color of ray florets, lower surface*.—Closest to RHS 155D but pure white.

Mature inflorescence:

*Diameter*.—12-13.5 cm.

*Depth*.—3.5 cm.

*Total diameter of disc*.—Not visible.

*Receptacle color*.—RHS 145B.

*Receptacle height*.—0.7 cm.

*Receptacle diameter*.—0.9-1.1 cm.

Ray florets:

*Average quantity of florets*.—About 150 in numerous whorls.

*Color of florets, upper surface*.—Closest to RHS 155D but pure white.

*Color of florets, lower surface*.—Closest to RHS 155D but pure white.

*Length*.—5.5-5.8 cm.

*Width*.—0.8-1.0 cm.

*Shape*.—Mostly spoon-shaped.

*Apex shape*.—Obtuse.

*Base shape*.—Cuneate.

*Margin*.—Entire.

*Texture, upper surface*.—Papillose.

*Texture, lower surface*.—Papillose.

Disc florets:

*Average quantity of florets*.—About 40.

*Color of florets*.—RHS 155C basally with RHS 5B apex.

*Length*.—0.6 cm.

*Width*.—0.1 cm.

*Shape*.—Tubular, elongated.

*Apex shape*.—Acute, 5 pointed.

*Texture, inner surface*.—Glabrous.

*Texture, outer surface*.—Glabrous.

Phyllaries:

*Quantity*.—About 40.

*Color, upper surface*.—RHS 137B to RHS 137C.

*Color, lower surface*.—RHS 137C.

*Length*.—0.9-1.0 cm.

*Width*.—0.25 cm.

*Shape*.—Lanceolate.

*Apex shape*.—Acute.

*Based*.—Fused.

*Margins*.—Entire with papery margins.

*Texture, upper surface*.—Glabrous.

*Texture, lower surface*.—Bifid T-shaped hairs.

Reproductive organs:

*Pistil.*—1, found on both types of florets.
*Length.*—0.7 cm.
*Style color.*—A little lighter than RHS 1C.
*Style length.*—0.65 cm.
*Stigma color.*—RHS 1B.
*Stigma shape.*—Bi-parted.
*Ovary color.*—RHS 155C.
*Ovary length.*—0.1 cm.
*Ovary width.*—0.05 cm.
*Stamens.*—4, found on only on the disc florets.
*Color of filaments.*—RHS 1C.
*Length filaments.*—0.4-0.5 cm.
*Anther color.*—RHS 13C.
*Anther length.*—0.15-0.2 cm.
*Anther shape.*—Oblong.
*Color of pollen.*—RHS 14B.
*Pollen amount.*—Low.
*Fertility/seed set.*—Has not been observed to date.
*Disease/pest resistance.*—Has not been observed to date.

What is claimed is:

1. A new and distinct variety of *Chrysanthemum* plant named 'CIDZ0047' substantially as illustrated and described herein.

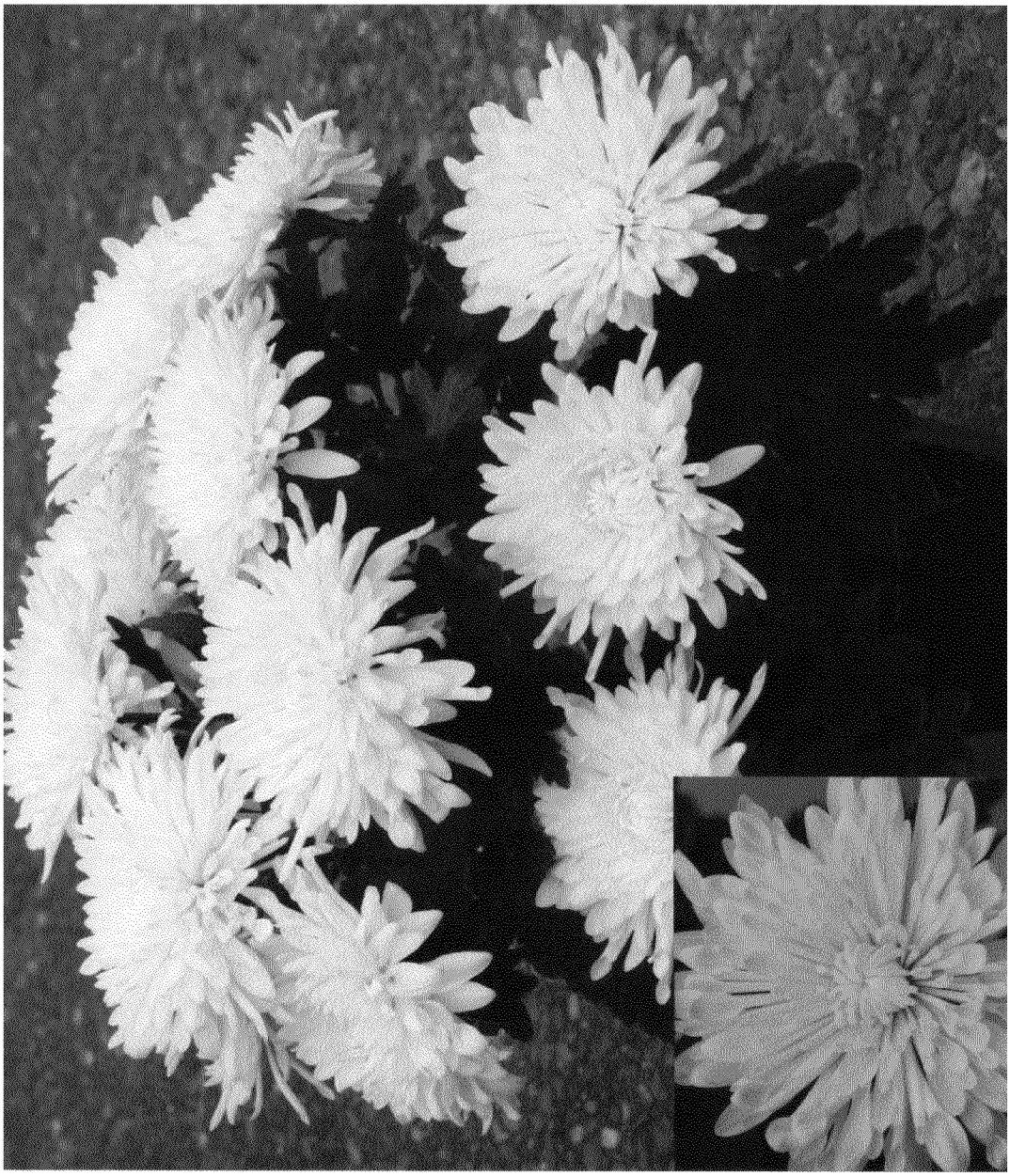

* * * * *